United States Patent [19]

Nolan et al.

[11] 4,265,714

[45] May 5, 1981

[54] GAS SENSING AND MEASURING DEVICE AND PROCESS USING CATALYTIC GRAPHITE SENSING ELECTRODE

[75] Inventors: Mary E. Nolan, Topsfield; John A. Kosek, Danvers; Anthony B. La Conti, Lynnfield, all of Mass.

[73] Assignee: General Electric Company, Wilmington, Mass.

[21] Appl. No.: 133,163

[22] Filed: Mar. 24, 1980

[51] Int. Cl.³ .......................................... G01N 27/52
[52] U.S. Cl. ................................ 204/1 T; 204/195 S
[58] Field of Search ............... 204/195 S, 195 R, 1 T, 204/1 B, 1 N, 1 K; 324/464, 465, 425; 422/98

[56] References Cited

U.S. PATENT DOCUMENTS

| | | |
|---|---|---|
| 3,134,697 | 5/1964 | Niedrach . |
| 3,432,355 | 3/1969 | Niedrach et al. . |
| 3,776,832 | 12/1973 | Oswin et al. ........................ 204/195 R |
| 3,824,167 | 7/1974 | Oswin et al. ........................ 204/195 R |
| 3,992,271 | 11/1976 | Danzig et al. .......................... 204/129 |
| 4,001,103 | 1/1977 | Blurton et al. ..................... 204/195 R |
| 4,042,464 | 8/1977 | Blurton et al. ........................ 204/1 T |
| 4,052,268 | 10/1977 | Blurton et al. ........................ 204/1 T |
| 4,123,700 | 10/1978 | La Conti et al. ............. 204/195 S X |
| 4,171,253 | 10/1979 | Nolan et al. ........................ 204/195 S |
| 4,197,177 | 4/1980 | Proctor ............................. 204/195 R |

OTHER PUBLICATIONS

J. M. Sedlak et al., J. Electrochem. Soc., pp. 1476-1478, Oct. 1976.

"The Condensed Chemical Dictionary", Eighth edition, p. 426, (1971).

Primary Examiner—G. L. Kaplan
Attorney, Agent, or Firm—I. David Blumenfeld

[57] ABSTRACT

A gas detecting and measuring device and method highly selective for the detection of certain gases is described. The gas detector is capable of detecting and measuring a gas which can be electrochemically oxidized or electrochemically reduced at a voltage of between about 0.6 and 1.5 volts relative to a standard hydrogen electrode. The gas detecting and measuring device and process are highly selective for the oxides of nitrogen ($NO_x$) and chlorine. The gas detecting device utilizes a hydrated, solid polymer electrolyte ion transporting membrane in electrical contact with an improved catalytic graphite sensing electrode. For detecting an oxidizable gas such as nitric oxide (NO), an improved graphite anode in contact with the solid polymer electrolyte is used with a cathode and a reference electrode as an electrochemical cell, and for detecting a reducible gas such as chlorine ($Cl_2$) or nitrogen dioxide ($NO_2$), an improved graphite cathode is used with an anode and a reference electrode as an electrochemical cell. Under an applied voltage, oxidizable gas is oxidized at the graphite anode and is detected or measured by a suitable circuit as a result of the current generated by the oxidation reaction, or reducible gas is reduced at the graphite cathode and is detected or measured by a suitable circuit as a result of the current generated by the reduction reaction.

41 Claims, 7 Drawing Figures

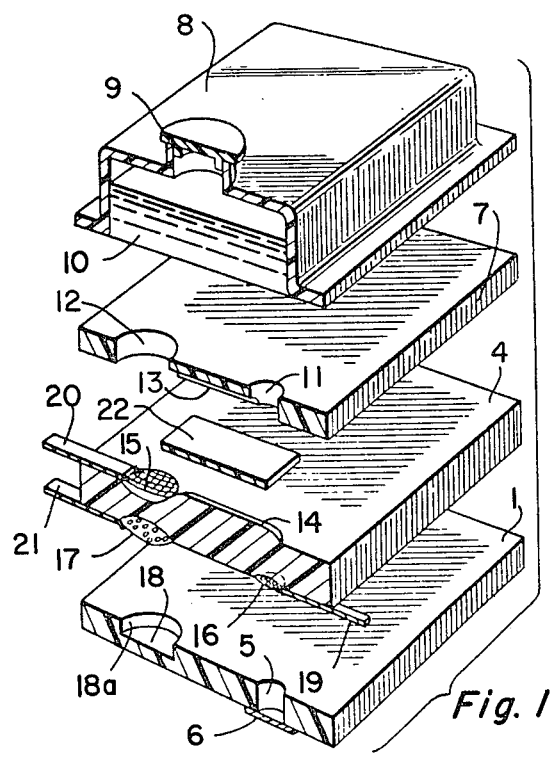
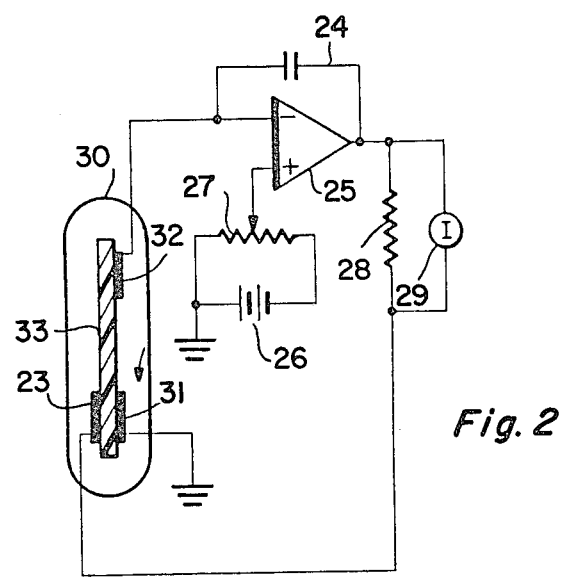

APPLIED VOLTS VS. STANDARD HYDROGEN ELECTRODE

GAS SENSING AND MEASURING DEVICE AND PROCESS USING CATALYTIC GRAPHITE SENSING ELECTRODE

This invention relates generally to a gas detecting and measuring apparatus and process, and more particularly, the invention relates to the detection and measurement of gases which are electrochemically oxidized or electrochemically reduced at a selected constant voltage in an electrochemical sensor which utilizes a three-electrode hydrated, solid polymer electrolyte.

Electrochemical devices to detect and measure various gaseous constituents such as hydrogen, oxygen, carbon monoxide, nitric oxid, nitrogen dioxide, and the like are well known and have been described in various publications and patents. An electrochemical gas sensing device is defined as a sensor in which the gaseous constituents to be detected or measured are brought in contact with a catalytic sensing electrode so that the constituent is either electrochemically oxidized or reduced with the exchange of electrons. The flow of current due to the oxidation and reduction of the gaseous constituent is then a measure of the concentration of the constituent to be detected.

Many of the well-known electrochemical gas-sensing devices utilize corrosive liquid electrolytes and are thus subject to electrolyte leakage, masking or fouling of electrodes and catalyst sites at which the electrochemical conversion of the gas takes place and changing electrolyte concentrations during operation. These characteristics of the liquid electrolyte gas sensing systems seriously affect the performance of the sensor in terms of its sensitivity and response. Furthermore, the liquid electrolytes used in these prior art gas sensor systems offen cause the destruction or dissolution of expensive metal electrodes. For example, silver used in an electrode maintained at a potential of 0.7 volts versus a standard hydrogen electrode, dissolves in the liquid electrolyte even when the system is maintained on open circuit. In other cases, catalytic gold deposited as a layer directly upon a sheet support or gold mixed with a suitable binder and applied to a suitable support such as polytetrafluoroethylene, carbon or a metal, has been used as the anode of an electrochemical cell for catalyzing the electrooxidation of nitric oxide and nitrogen dioxide. However, with electrodes comprising gold, there is some undesirable oxygen oxidation/reduction.

In one prior art embodiment, a sensing electrode comprising a carbon-supported gold catalyst has been used in an electrochemical sensing device comprising an electrochemical cell having a sensing electrode, a counter electrode and an aqueous electrolyte in contact with the sensing electrode and counter electrode. Generally, the catalytic activity of carbon supported gold is equivalent to, but no better than, non-supported gold, however, realtive to the electron-oxidation of carbon monoxide, it is disclosed in the prior art that the catalytic activity of the carbon supported gold electrodes was less than that of unsupported gold electrodes. Thus, the carbon supported gold electrode may demonstrate better selectivity when carbon monoxide is present in the gas that is being detected, however, carbon supported gold electrodes are generally of lesser sensitivity in the detection of the noxious gases. Furthermore, when utilized for nitric oxide detection at high anodic potentials, there is some anodic dissolution of the gold (at greater than 1.1 volts potential versus a standard hydrogen electrode). There is also some oxidation of interfering gases such as ethylene, acetylene, and oxygenated hydrocarbons especially at temperatures above ambient. Another disadvantage of the gas sensors which utilize gold or carbon supported gold as electrodes for cathodic reduction for the detection of such gases as nitrogen dioxide, is the potential interference from oxygen from the air at cathodic potentials of 0.8 volts or below versus a standard hydrogen electrode. This is aggravated by temperatures above ambient. Attempts to use non-noble metals, such as silver, results in considerable dissolution when the electrochemical cell is left on open circuit as described above.

Electrochemical gas sensors for carbon monoxide, oxides of nitrogen, alcohol, and the like, characterized by the use of a potentiostated cell utilizing a hydrated, solid polymer electrolyte membrane, have been described in the prior art. The electrochemical cell having the solid polymer electrolyte membrane, is used in an electrically biased mode, along with a potentiostatic system to maintain a cell sensing electrode at the correct potential to obtain rapid oxidation of the gas to be sensed while at the same time avoiding interference from air due to reduction of oxygen or interference due to the dissociation of water. In these systems, the counter electrode side of the solid polymer electrolyte membrane is flooded with distilled water so that incoming gases are brought essentially to 100% relative humidity by rapid vapor phase water transport across the membrane. These gas detectors having the solid polymer electrolyte membranes include an ionically conductive hydrated, solid polymer electrolyte bridge formed on one side of the membrane spatially oriented with respect to the reference and sensing electrodes to provide a low-resistance path between these electrodes. These electrochemical cells exhibit high output, excellent stability and high sensitivity to the gases to be detected. The sensing and reference electrodes of these electrochemical cells are positioned in such a manner that the reference electrode is positioned outside of the current flux field of the sensing electrode. As a result, the temperature characteristics of the cell are substantially more stable than those of other devices. The catalytic electrodes of these devices are preferably gas permeable, noble metal alloyed particles bonded through particles of a hydrophobic polymer such as polytetrafluoroethylene. Catalytic electrodes preferred for carbon monoxide oxidation are preferably a bonded mixture of reduced oxides of a platinum-5% iridium alloy and polytetrafluoroethylene hydrophobic particles. Although the foregoing electrochemical cells having solid polymer electrolyte membranes overcome the disadvantages of the electrochemical devices and processes utilizing liquid electrolytes, there is a need for long-life gas detecting and measuring instruments which are highly selective to certain noxious gases such as nitric oxide, nitrogen dioxide, chlorine and the like, with no interference from carbon monoxide, acetylene and ethylene for monitoring ambient air where diesel fuels are used, or where high temperature oxidation of a hydrocarbon type fuel in ambient air occurs, such as in welding operations.

It is, therefore, a principal object of the instant invention to provide a gas-detecting and measuring apparatus and process using electrochemical cells having solid polymer electrolyte ion transporting membranes which are capable of detecting and measuring such noxious gases as the oxides of nitrogen ($NO_x$) and chlorine ($Cl_2$)

with no interference from carbon monoxide, acetylene, ethylene and the like.

It is another object of this invention to provide a gas sensing device and process which utilizes an inexpensive electrode material with excellent selectivity as well as excellent sensitivity to the noxious gases being detected.

Still another object of this invention is to provide an electrochemical gas detecting and measuring device and process for detecting specified noxious gases without the use of liquid electrolytes and without sensitivity to carbon monoxide gas.

A further object of this invention is to provide an electrochemical gas detecting and measuring device and process for detecting specified noxious gases without the use of liquid electrolytes and without sensitivity to carbon monoxide gas.

Another object of this invention is to provide an electrochemical gas-sensing device and process in which there is no dissolution of metal at the catalytic sensing electrode.

Other objects and advantages of the instant invention will become apparent from the following detailed description.

The objects and advantages of this invention are realized in an electrochemical gas-sensing device of the solid polymer electrolyte type in which a catalytic graphite sensing electrode along with a reference electrode are positioned on one side of an ion transporting membrane and a counter electrode is positioned on the other side of the membrane opposite the catalytic graphite sensing electrode. Thus, there is provided in an electrochemical gas-sensing device of the type having a hydrated, solid polymer electrolyte ion transporting membrane, catalytic sensing and reference electrodes positioned on one side of the membrane and in a counter electrode positioned on the opposite of the membrane, the electrodes being bonded to the ion transporting membrane, means for exposing the sensing electrode to a gas to be sensed and means for measuring a current which flows between the sensing and counter electrodes while a voltage applied to the sensing electrode is maintained constant, the improvement being a sensing electrode comprising graphite bonded to the solid polymer electrolyte ion transporting membrane.

In accordance with the present invention, there is also provided a method for the electrochemical detection of a gas comprising the steps of (a) passing a gaseous sample containing the gas to a catalytic graphite sensing electrode in an electrochemical gas-sensing cell having a hydrated, solid polymer electrolyte ion transporting membrane, a catalytic sensing electrode and a reference electrode positioned on the opposite side of the membrane, said electrodes being bonded to the ion transporting membrane; (b) maintaining a catalytic graphite sensing electrode at a constant applied voltage; and (c) detecting current flow between the catalytic sensing electrode and the counter electrode.

It has been found in accordance with the present invention that when means is provided for selectively applying a voltage to the sensing electrode at a fixed potential within a range of about 0.7 to about 1.3 volts versus a standard hydrogen electrode, select gases such as nitrogen dioxide ($NO_2$), nitric oxide (NO), and chlorine ($Cl_2$) can be detected and measured without interference from carbon monoxide (CO), air ($O_2$) and hydrocarbon gases ($C_2H_2$, $C_2H_4$, etc.). As will be explained in detail below, a fixed potential must be selected for the particular gas being detected and/or measured, and in certain cases if several of the noxious gases are present, it is necessary to provide means for filtering such noxious gas or gases which cause a current flow between the sensing and counter electrodes at the same potential as the gas being detected. At cathode potentials below about 0.7 volts or anode potentials above, about 1.3 volts, it has been found that compensating means can be provided to compensate for current due to air (oxygen) in the electrochemical gas-sensing cell having a catalytic graphite sensing electrode.

A typical gas sensor which may be adapted in accordance with the present invention by incorporating a catalytic graphite sensing electrode in electrical contact with a hydrated, solid polymer electrolyte, is disclosed in U.S. Pat. No. 4,171,253. A typical potentiostatic circuit for controlling operation of the cell and maintaining the reference and sensing electrode at a desired potential is also illustrated in U.S. Pat. No. 4,171,253.

The novel features which are believed to be characteristic of this invention are set forth in the appended claims. The invention itself, however, both as to organization and mode of operation, together with further objectives and advantages thereof are best understood by reference to the following description taken in connection with the accompanying drawings described below.

FIG. 1 is an exploded, sectional view of a three-electrode electrochemical gas sensor cell utilizing a solid polymer electrolyte and having the improved graphite catalytic sensing electrode of the present invention.

FIG. 2 is a schematic diagram showing the gas sensing cell and a potentiostatic circuit for controlling operation of the cell and maintaining the reference and sensing electrodes at a desired potential.

Figure 3:
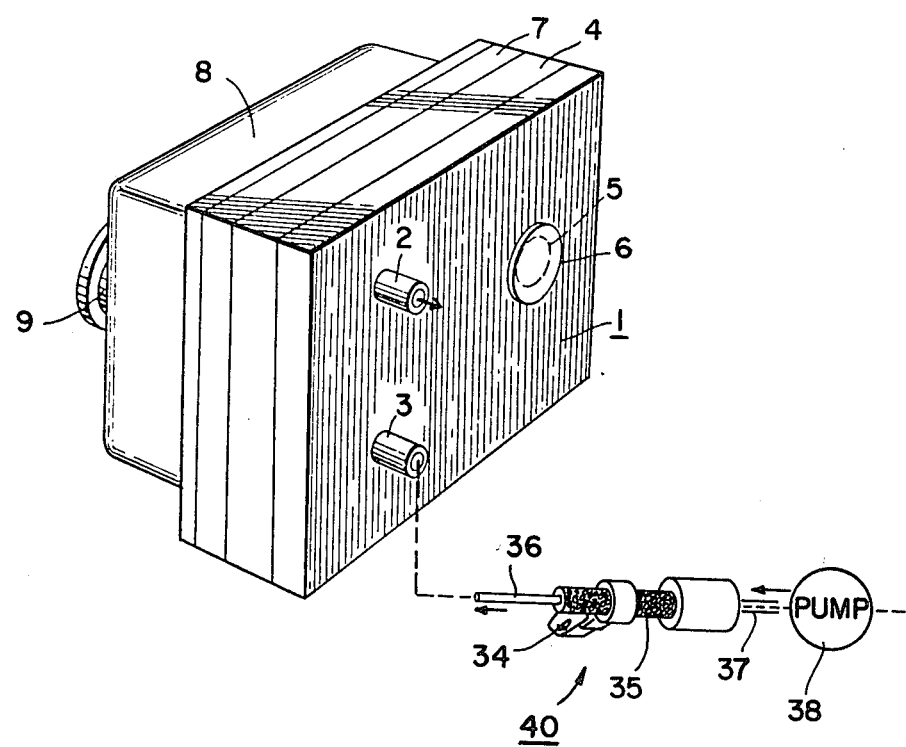
FIG. 3 is a perspective view of an electrochemical cell in its assembled condition.

Operation of the electrically biased, potentiostated three-electrode electrochemical gas sensor is based upon the oxidation or reduction of the constituent to be detected or measured at the catalytic graphite sensing electrode. The catalytic graphite sensing electrode is maintained at a potential to produce rapid oxidation when the detection or measurement of such gases as nitric oxide (NO) is desired. At these potentials at which oxidation occurs, the graphite sensing electrode is an anode, and the oxidation is referred to as anodic oxidation. The catalytic graphite sensing electrode is maintained at a potential to produce rapid reduction when the detection or measurement of gases such as nitrogen dioxide ($NO_2$) or chlorine ($Cl_2$) is desired. At these potentials, the graphite sensing electrode is a cathode, and the reduction is referred to as cathodic reduction. As will be noted in FIG. 4, at the potential (applied voltage) between about 0.7 and about 1.3 volts useful for the purposes of the present invention, oxygen ($O_2$) or air (FIG. 4b) and carbon monoxide (CO) (FIG. 4c), do not affect the analytical sensitivity of the electrochemical gas sensor having the catalytic graphite sensing electrode. At an applied potential below about 0.7 volt and above about 1.3 volts, optional compensating means may be used to correct or compensate for background current due to oxygen.

A typical electro-oxidation in the sensor cell having the catalytic graphite sensing electrode in electrical contact with the hydrated, solid polymer electrolyte membrane is that of nitric oxide (NO):

$$NO + H_2O \rightarrow NO_2 + 2H^+ + 2e^-$$

Water vapor (H$_2$O) is provided through the hydrated, solid polymer electrolyte membrane and may be continuously replenished from a suitable reservoir.

A typical electro-reduction in the sensor cell having the catalytic graphite sensing electrode in electrical contact with the hydrated, solid polymer electrolyte membrane is that of nitrogen dioxide (NO$_2$):

$$NO_2 + 2H^+ + 2e^- \rightarrow NO + H_2O$$

The reference, sensing and counter electrodes of the cell are maintained at the desired potentials, and current flow between the anode and cathode (sensing and counter electrodes) is measured by means of a suitable circuit, such as potentiostatic circuitry, briefly described below and well known in the prior art. Thus, this circuitry is means for selectively applying a voltage to the sensing electrode at a fixed potential within the range of about 0.7 to about 1.3 volts versus a standard hydrogen electrode. It is to be understood that the terms sensing, detecting, and measuring of the gases can be used interchangeably herein, and that the present invention can be adapted by suitable electronic circuitry to sense or detect as well as quantitatively measure the concentration of one or more gaseous constituents in a stream or sample of gas.

For the electrochemical reduction of gas, e.g., nitrogen dioxide (NO$_2$), the gas sensing device has a catalytic graphite sensing cathode and a reference electrode on one side of a solid polymer electrolyte ion transporting membrane and an anode on the other side of the membrane. The electrodes are in electrical contact with the membrane, generally by bonding the electrodes to the membrane. For the electrochemical oxidation of a gas, e.g., nitric oxide (NO), the gas sensing device has a catalytic graphite sensing anode and a reference electrode on one side of a solid polymer electrolyte ion transporting membrane and a cathode on the other side of the membrane. The electrodes are in electrical contact with the membrane, generally by bonding the electrodes to the membrane.

FIG. 1 illustrates a typical electrochemical gas sensor cell in which the catalytic graphite sensing electrode of the present invention may be used. The cell is illustrated in an exploded, sectional view so that the parts thereof can be clearly viewed and so that the catalytic graphite sensing electrode of the present invention is clearly shown. In essence, FIG. 1 is shown in U.S. Pat. Nos. 4,123,700 and 4,171,253.

In FIG. 1, the sensing cell is one of the self-humidifying type described in the prior art including the above referenced patents. The cell includes a reservoir 8 which is filled with distilled water 10 through closable port 9 and is in firm contact with the upper surface of gasket 7. Gasket 7 contains a pair of hydration ports 11 and 12 connected, on the underside of gasket 7, by means of a water channel 13. Channel 13 is located over an ionically conductive, hydrated bridge 14 formed integrally along the upper surface of a hydrated, solid polymer electrolyte cation exchange membrane 4.

Thus, bridge 14 extends from counter electrode 15 to a point directly opposite a catalytic reference electrode 16, bonded to and embedded in the lower surface of membrane 4. Hydration port 12 is somewhat smaller in area than counter electrode 15. The surface of the counter electrode is flooded by distilled water from the reservoir 8. Consequently, water in vapor phase diffuses rapidly through the membrane to the other side in the vicinity of a catalytic graphite sensing electrode 17 which is also bonded to the lower surface of membrane 4 and is in spatial alignment with counter electrode 15.

A gas stream containing the constituent or constituents to be detected and/or measured is brought into a circular chamber 18 in the surface of a bottom plate 1 through opening 18a. A sampling pump or other device (not shown) brings the gas sample into the chamber through opening 18a. The gas sample in chamber 18 is thus brought into contact with catalytic graphite sensing electrode 17. Reference electrode 16 which is also bonded to the underside of membrane 4, is in direct communication with an opening 5 which is covered by a Teflon or other suitable barrier film 6. Film 6 permits passage of oxygen or air to the reference electrode 16 while blocking the gaseous constituent or constituents which are to be sensed as, for example, nitric oxide, nitrogen dioxide, chlorine and the like. That is, access to reference electrode 16 is through film 6 which selectively blocks the gaseous constituent or constituents to be detected. A Teflon barrier film is generally appropriate for blocking most of the noxious gases without blocking the oxygen or air. However, in certain instances it may be desirable to use a different film material or a combination of film materials, e.g., silicone rubber, for this barrier, depending upon the gases to be excluded. One skilled in the art can select the appropriate material for this purpose. Each of the electrodes has suitable conductive tabs 19, 20 and 21. These tabs are connected to the appropriate circuitry such as potentiostatic circuitry, associated with the cell and briefly described relative to FIG. 2.

An adhesive tape 22 is positioned between gasket 7 and membrane 4 at a location away from the electrodes and hydrated bridge 14 in order to fasten the gasket 7 and membrane 4 securely together. A similar adhesive tape, not shown, is positioned between the lower surface of membrane 4 and the bottom plate 1. This tape is located between electrodes 16 and 17 to secure the membrane to the bottom plate and to block flow of gas between the reference and sensing electrodes. This, of course, may be achieved other than by means of an adhesive tape, although an adhesive tape is a simple and ready solution to the problem. The reservoir 8, reservoir port 9, plate 1 and gasket 7 may be made of any suitable material. One preferred construction material is a thermoplastic polycarbonate resin produced by reacting bisphenol A and phosgene known commercially as Lexan. Lexan is a trademark of General Electric Company.

The swollen, hydrated, ionically conductive bridge 14 extends along the lateral surface of the membrane from electrode 15 to a point on the upper surface which is spatially aligned with reference electrode 16 which contacts the lower surface of membrane 4, in order to provide a good, ionically conductive path from catalytic graphite sensing electrode 17 which is aligned with counter electrode 15. This path is then from catalytic graphite sensing electrode 17 through membrane 4 to counter electrode 15 along bridge 14 through membrane 4 and to reference electrode 16. This provides a low-resistance path between the reference and catalytic graphite sensing electrodes substantially eliminating or minimizing IR drop between the catalytic graphite sensing electrode 17 and reference electrode 16. As a result, the sensitivity is high so that it produces a high output even with very low gas concentrations. Furthermore, the output is highly invariant with time and is not subject to background current errors at zero air operation due to temperature changes. The cell is also constructed so that the catalytic graphite sensing electrode 17 and reference electrode 16 are on the same side of the membrane. They are positioned as closely together as possible, while at the same time making sure that the reference electrode 16 is not affected by the current flux lines between the catalytic graphite sensing electrode 17 and counter electrode 15 as the potentiostatic circuit drives current from the counter electrode 15 to the catalytic graphite sensing electrode 17 to maintain the electrode potential and the voltage differential constant.

The solid polymer electrolyte, ion exchange membrane 4, characterized by ion transport selectivity and otherwise referred to herein as hydrated, solid polymer electrolyte ion transporting membrane, is preferably a perfluorocarbon sulfonic acid membrane which has excellent ion exchange capacity, has high stability, is resistant to acids and strong oxidants, and has excellent thermal stability. These solid polymer electrolyte ion exchange membranes are well known in the prior art and are described in the above referenced patents. Being a cation exchange membrane, it permits passage of positively charged ions, i.e., cations, and rejects and blocks passage of negatively charged ions, i.e., anions. One preferred form of such a cation membrane is one in which the polymer is a hydrated co-polymer of polytetrafluoroethylene (PTFE) and polysulfonyl fluoride vinyl ether containing pendant sulfonic acid groups. One form of such a solid polymer electrolyte is sold commercially by E. I. Dupont and Company under the trade designation "NAFION". Another class of cation exchange resins are those where the ion exchanging group is —COOH pendant from the backbone of the polymer. The membranes may be hydrated by soaking them in water, e.g., in water at 100° C. for about 30 minutes. In one embodiment, the membranes are soaked in water at room temperature and then at 40° C. for about 30 minutes. This yields a hydrated membrane having about 30–40% water based upon the dry weight of the membrane.

Electrodes 15, 16 and 17, are integrally bonded to the surface of the ion exchange membrane (ion transporting membrane). They are preferably in the form of decals of the appropriate catalytic material mounted on current collecting screens. In accordance with the present invention, the catalytic sensing electrode is made of carbon, preferably graphite. The catalytic electrodes are preferably gas permeable. Except for the catalytic graphite sensing electrode, the other electrodes, i.e., counter electrode 15 and reference electrode 16 are preferably noble metal alloyed particles bonded to particles of a hydrophobic polymer such as polytetrafluoroethylene. The counter electrode 15 and reference electrode 16 are preferably a bonded mixture of reduced oxides of a platinum/5% iridium alloy or a platinum black and polytetrafluoroethylene (PTFE) hydrophobic particles. These are generally made by a modified Adams method as described in U.S. Pat. No. 4,171,253.

Other suitable catalytic electrode materials well known in the art may be used for counter electrode 15 and reference electrode 16. Reference is hereby made to U.S. Pat. No. 3,992,271 for a detailed description of a fabrication process for the reduced oxides of platinum-/iridium alloys.

The catalytic sensing electrode preferably comprises graphite, although other forms of conductive carbon such as carbon black, may be used. In the preferred embodiments, the graphite is bonded to particles of a hydrophobic polymer such as polytetrafluoroethylene. One of the preferred graphites which may be used in the catalytic graphite sensing electrode of the present invention, is a powdered graphite commercially known as POCO Graphite 1748 obtained from Union Oil Company. POCO is a trademark of Poco Graphite, Inc. for a series of fine-grained high strength isotropic formed graphite materials of three basic density grains ranging between 1.50 and 1.88 grams per $cm^3$. As indicated above, the powdered graphite is perferably mixed with polytetrafluoroethylene particles (Teflon). One suitable form of the polytetrafluoroethylene is sold by E. I. Dupont Company under the trade designation, Teflon T-30. Teflon is a trademark of E. I. Dupont and Company.

As indicated above the catalytic sensing electrode may comprise the carbon material, preferably graphite, alone or in combination with other materials such as binders, inert fillers, inert adjuvants, or additives. The preferred catalytic sensing electrode comprises graphite homogeneously blended with about 10–50 percent by weight of the graphite and polymer, and more preferably 10–25 percent by weight of the graphite and polymer.

The method of bonding of the carbon material to the solid polymer electrolyte (cation exchange membrane) to form electrical contact therewith is not critical. However, several preferred methods are well-known in the art. One such method is to place the graphite or homogeneous blend of graphite and fluorocarbon polymer in a mold followed by the application of heat until the composition is sintered into a decal form which is then bonded to and embedded in the surface of the membrane by the application of pressure and heat. Various methods may be used to bond and/or embed the electrode into the membrane, including the one described in detail in U.S. Pat. No. 3,134,697 wherein the electrode structure is forced into the surface of a partially polymerized ion exchange membrane, thereby integrally bonding a sintered, porous, gas absorbing particle mixture to the membrane and embedding it in the surface of the membrane. Another fabricating process is described in detail in U.S. Pat. No. 3,432,355. As used herein, bonding the electrode to the membrane surface means any electrical contact between the membrane and the electrode material and includes contact between electrode decals and the membrane or the embedding of electrode material in the surface of the membrane.

The amount of carbon material, e.g., graphite, bonded to the solid polymer electrolyte ion exchange or transporting membrane is not critical. However, there is a preferred amount of the carbon material, e.g., graphite, which may be placed upon the ion transporting membrane to make the catalytic sensing electrode. The minimum loading of graphite is about four milligrams of graphite per centimeter square of membrane surface. Loadings of less than 4 mg per $cm^2$ are generally not recommended because of the loss of structural integrity of the electrode. Because of the present methods used in pressing the catalytic graphite sensing material upon current collector screens, the lower limit of the graphite loading is generally limited to the above-described loading. Although lesser loadings of the graphite may be operable, the compromise of structural integrity dictates against loading the graphite at less than 4 mg per $cm^2$. A preferred graphite loading is within the range of 4 mg per $cm^2$ to about 10 mg per $cm^2$ with the most preferred loading being about 6 mg per $cm^2$. Although the upper thickness or loading of the graphite is not critical, loadings of graphite greater than 500-100 mg per $cm^2$ are operable. Furthermore, in certain cases, increased loadings of graphite may cause "background" readout problems which may be indicative of high IR values. Further, excessive loadings of the graphite may also increase the length of time for the electrochemical reaction to take place, thereby creating slower response time.

FIG. 2 illustrates schematically an arrangement in which the electrodes of a solid polymer electrolyte-type gas sensor having the catalytic graphite sensing electrode in accordance with the present invention, are coupled to a potentiostatic circuit which maintains the potential at the sensing electrode constant at the desired level and maintains the proper potential difference between the sensing and the reference electrodes. Potentiostatic devices are well known in the art and only a brief description thereof will be provided in connection with FIG. 2 for the sake of completeness. In accordance with the present invention, any suitable means may be provided for measuring the current flow between the sensing and counterelectrodes while maintaining the voltage applied to the sensing electrode constant. The solid polymer electrolyte ion exchange (transport) membrane 33 having catalytic graphite sensing electrode 31, a reference electrode 32 on one side of the membrane and a counter electrode 23 on the other side of the membrane. The reference electrode 32 is coupled to the inverting input terminal of an operational amplifier 25 and is compared to a reference voltage from a DC supply source 24 which is applied to the non-inverting input of amplifier 25. DC source 24 includes a battery or other power source 26, the positive terminal of which is grounded. Potentiometer resistor 27 is connected across battery 26 and has a slider which is connected to the non-inverting terminal. The position of this slider is so adjusted to represent the potential at which the sensing electrode is to be maintained. The potentiostatic circuit thus shown in FIG. 2 senses any change in the voltage between the reference and sensing electrode and compares it to the preset value at the potentiometer slider. Any changes are used to generate a current at the output of operational amplifier 25 between counter electrode 23 and catalytic graphite sensing electrode 31 to eliminate the difference voltage producing it. The output current is sensed across resistor 28 by a suitable meter 29.

The current required to drive the system back to null balance is representative of the concentration of the gas being sensed. That is, as a gas such as nitric oxide, is oxidized to nitrogen dioxide ($NO_2$), and the electrons are liberated by electrochemical oxidation, the potential at the sensing electrode tends to shift as does the differential voltage. A current is generated to drive the system through a negative feedback mode back to its null point, mainly to maintain the sensing electrode at the selected voltage between about 1.1 volts and 1.45 volts and the differential voltage between the reference and sensing voltage at plus 300 mv. The current required to do so is then a direct indication of the gas concentration since it is the oxidation of the gas which has produced the change in the differential voltage which requires a shift in the current to drive the system back to the null balance. An identical system is used for the determination of the concentration of a gas being sensed when there is a cathodic reduction except the catalytic graphite sensing electrode is maintained at a different voltage. Therefore, the current required to maintain the catalytic graphite sensing electrode at the designated voltage for the electrochemical reduction (cathodic reduction) and the differential voltage between the reference and catalytic sensing voltage at minus 150 mv is a direct indication of the gas concentration since it is the reduction of the gas which has produced the change in the differential voltage which requires a shift in the current to drive the system back to null balance.

Figure 5:
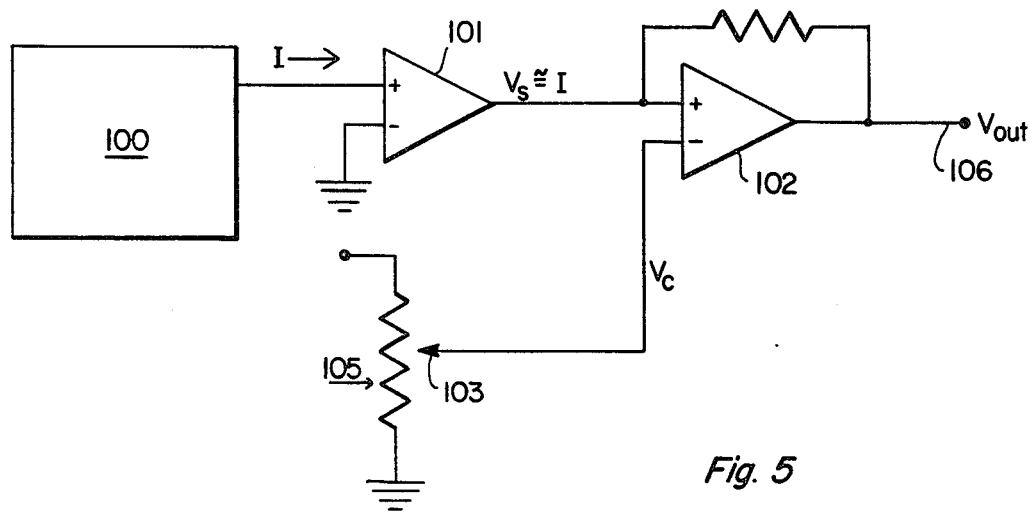
FIG. 5 is a schematic diagram showing an automatic compensating circuit which may be optionally used in accordance with the present invention.

Generally it is preferred to limit the upper voltage to a maximum of 1.3 volts to avoid oxidation of the water in the membrane since this water reaction competes with the oxidation of the nitric oxide or other oxidizable gas and introduces current flow which has produced errors in the sensing of the gas concentration. However, means can be provided for compensating for any background current due to oxygen or any other gas. In FIG. 5, discussed below, an automatic compensating circuit is shown for compensating for background current due to oxygen below 0.7 volt or above 1.3 volts.

In the event multiple interfering gases are present in the composition of gases being analyzed, it may be necessary to filter certain of the interfering gases from those gases to be analyzed. Interfering gases are defined herein as those gases which produce a response in current flow at the applied voltage or within the applied voltage range or overlapping with the applied voltage at which the gas or gases being analyzed, measured and/or detected also cause the current flow. Thus, the interferant gas or gases register a response or analytical selectivity at the same potential as the gas or gases being analyzed, detected and/or measured in the electrochemical cell. For example, if the gas to be detected and/or measured causes a current flow at an applied voltage of 1.3 volts versus a standard hydrogen electrode, and a gas which is present in the gas to be measured and/or detected also caused a current flow at the same applied voltage or overlaps with that applied voltage, then it will be necessary to filter such an interfering gas from the gas to be measured and/or detected if it is not compensated for by a suitable compensating means.

An examination of FIG. 4 demonstrates that carbon monoxide (CO) and air ($O_2$) do not interfere with the analytical selectivity of gases detected and/or measured at the designated applied voltages when the catalytic graphite sensing electrode is used in accordance with the present invention. Background current due to air ($O_2$) and certain other gases can be corrected for (compensated for) by any suitable means.

One such compensating means is illustrated in FIG. 5. In FIG. 5, an automatic compensating circuit is illustrated for correcting for current due to air ($O_2$). The circuit of FIG. 5 is a means for correcting or compensating for any background current. Thus, when the sensing device of this invention is used to detect and/or measure, e.g., nitrogen dioxide gas, the circuit of FIG. 5 can correct for, or compensate for, any background current. Thus, when the sensing device of this invention is used to detect and/or measure, e.g., nitrogen dioxide gas, the circuit of FIG. 5 can correct for, or compensate for, any background current due to air ($O_2$) below 0.7 volt. When the sensing device is used to detect and/or measure, e.g., nitric oxide gas, the circuit of FIG. 5 can correct for, or compensate for any background current due to air ($O_2$) above 1.3 volts.

In FIG. 5, the gas sensing device of the present invention is represented by 100. Amplifier 101 is connected to the current output of sensor 100 and converts current (I) from sensor 100 to a voltage Vs. The voltage (Vs) from amplifier 101 is approximately equal to the current (I) from sensor 100. Potentiometer 105 having adjustable potentiometer slider 103 is used to compensate for any undesirable current from sensor 100. For example, when sensor 100 detects an oxide of nitrogen at a potential which also detects another gas, e.g., oxygen, and the current output (I) from sensor 100 represents current from both the oxide of nitrogen and oxygen, potentiometer slider 103 at potentiometer 105 may be adjusted to correct for, or compensate for, the current due to the oxygen, and the resulting voltage output (Vout) at 106 represents the signal, response or voltage due only to the oxide of nitrogen.

Potentiometer slider 103, adjustable by a suitable shaft (not shown), may be used in the present invention at a cathode potential below about 0.7 volt or at an anode potential above about 1.3 volts to produce a compensating or correcting voltage (Vc) to correct for any undesirable current produced by sensor 100. Compensating voltage (Vc) can represent the sensor current due to the undesirable oxidation or reduction of oxygen at voltages above 1.3 volts or below 0.7 volts. The compensating voltage (Vc) is applied to the inverting terminal (−) of differential amplifier 102. Sensor voltage (Vs) from amplifier 101 (approximately equal to sensor current) is applied to the non-inverting terminal (+) of differential amplifier 102. In differential amplifier 102 compensating voltage (Vc) is substracted from sensor voltage (Vs) to produce the output voltage (Vout). Consequently, the output signal represents the voltage due only to the oxide of nitrogen being detected and/or measured and undesirable current due to other gases, e.g., air ($O_2$), has been eliminated or automatically compensated for, thereby permitting the operation of the sensing device of the present invention at a broader range of voltages.

In operation, sensor 100 is operated at a fixed applied voltage or potential to detect or measure a specific gas using the catalytic graphite sensing electrode of the present invention. The sensor current due to air ($O_2$) at that fixed voltage can be determined from Table III below, and the potentiometer slider 103 of potentiometer 105 can be adjusted to compensate for that current so that it is subtracted out of the sensor signal (current) at differential amplifier 102. For example, it can be seen that at a fixed voltage of 0.6 in Table III, the current due to air ($O_2$) is −46 microamps. The potentiometer slider 103 is appropriately set to provide a compensating voltage (Vc) equal to the −46 microamp current due to air ($O_2$). The compensating voltage (Vc) due to air at an applied voltage of 0.6 volt is subtracted from the sensor voltage (Vs) representing voltage due to both air and the gas being detected, in differential amplifier 102, and output voltage (Vout) at 106 represents the signal or voltage for only the gas being detected. In specific embodiments, this compensating device is especially useful for oxygen compensation when nitrogen dioxide gas is being detected or measured below about 0.7 volt and nitric oxide gas is being measured above about 1.3 volts. Other manual and automatic compensating means available in the prior art can also be easily adapted to carry out this function of compensating for undesirable gases.

It is also within the purview of one skilled in the art to use common filtration media to remove any interfering gases from a gas sample to be analyzed, detected and/or measured, and one skilled in the art can use any suitable prior art technique and material for selectively filtering the interfering gases from the gas sample or gas stream feeding into the catalytic graphite sensing electrode of the electrochemical cell in the gas sensing device. Table 1 below is a list of gases that could potentially interfere with a nitrogen dioxide ($NO_2$) analysis. Of all the gases tested, only hydrogen sulfide ($H_2S$), and sulfur dioxide ($SO_2$) had a significant response at an applied potential of −300 millivolts versus a Pt alloy black/$O_2$ reference electrode, and oxidation currents were observed for both gases. Neither of these gases gave a signal which was constant with time. After an initial response, the response to both gases slowly started to drift back to the background value. Exposure of the sensor cell to these gases ($H_2S$ and $SO_2$) did not have any effect on the response level to $NO_2$. Both of these gases may be filtered out by use of 0.1 molar mercuric chloride ($HgCl_2$) immobilized on filter paper.

TABLE I

INTERFERENCE LEVELS FOR INTERFERENT GASES $NO_2$ ANALYSIS

| Gas* | Gas Conc. (PPM) | Equivalent $NO_2$ Conc (PPM) | Interferent Ratio (PPM Interferent) (PPM $NO_2$) |
|---|---|---|---|
| $H_2S$ | 7.8 | 36 | 1/4.6 |
| $SO_2$ | 6.9 | 18 | 1/2.6 |
| $C_2H_2$ | 201 | 0 | — |
| $C_2H_4$ | 55 | 0 | — |
| NO | 20.8 | 0 | — |
| CO | 167 | 0 | — |
| **$H_2S$ | 5.7 | 0 | — |
| **$SO_2$ | 6.9 | 38 | 1/1.6 |

*All tests run without filter except where indicated
**Filter using 0.1 Molar aqueous $HgCl_2$ immobilized (dried upon) filter paper A review of the data in Table I shows that there is no interference from acetylene ($C_2H_2$), ethylene ($C_2H_4$), or nitric oxide (NO) as well as from carbon monoxide (CO) when nitrogen dioxide is being detected and/or measured in an electrochemical cell having a catalytic graphite sensing electrode in accordance with the present invention.

Table II is a list of gases which could potentially interfere with a nitric oxide (NO) analysis. It also lists the concentration of these gases which produce a signal equivalent to one part per million nitric oxide. Of all the gases tested, only hydrogen sulfide ($H_2S$) had an effect on the sensor cell performance, decreasing the response level by 0.2 microamps per PPM when the sensor cell has a catalytic graphite sensing electrode. Hydrogen sulfide and sulfur dioxide, as well as nitrogen dioxide, can be effectively filtered from the gas stream by use of triethanolamine. To prevent triethanolamine vapors from reaching the catalytic graphite sensing electrode surface and thereby rendering it insensitive to the nitric oxide gas, a short column of a suitable cation exchange resin material can be placed in the gas stream prior to the entrance of the gas into the sensor cell.

TABLE II

INTERFERENCE LEVELS FOR INTERFERENT GASES NO ANALYSIS

| Gas* | Gas Conc. (PPM) | Equivalent NO Conc. (PPM) | Interferent Ratio (PPM Gas) (PPM NO) |
|---|---|---|---|
| $H_2S$ | 7.8 | 2.8 | 2.6 |
| $SO_2$ | 9.3 | 0.9 | 10 |
| $NO_2$ | 6.6 | 17 | 1/2.5 |
| $C_2H_2$ | 201 | 0 | — |
| $C_2H_4$ | 55 | 0 | — |
| CO | 98 | 0 | — |
| **$H_2S$ | 78 | 0 | — |
| **$SO_2$ | 9.3 | 0 | — |
| **$NO_2$ | 6.6 | 0 | — |

*All tests run without triethanolamine filter except where indicated
**Triethanolamine filter used Since nitrogen dioxide would interfere with the detection and/or measurement of chlorine, it would be necessary to filter out the nitrogen dioxide from any stream of chlorine gas undergoing detection and/or measurement. Naturally, if there is no nitrogen dioxide present in the sample of chlorine gas, then no filtration is necessary.

The flow rate of the gas samples is not a critical aspect to the present invention, however, response, that is analytical selectivity for current flow in microamps, is directly dependent upon the flow rate. One skilled in the art can make the necessary adjustments and compensations for any inconsistencies, fluctuations or erroneous measurements due to flow rate. There is generally a preferred flow range of about 30-100 cc per minute and the most preferred flow rate is between about 60-80 cc per minute. Generally, flow rates for the passage of the sample to be analyzed through the sensor cell, that is across the catalytic graphite sensing electrode, in excess of about 120 cc per minute may cause the dehydration or drying of the catalytic graphite electrode surface. Generally, at flow rates lower than about 30 cc per minute, the signal or response may become too small for accurate detection and/or measurement.

FIG. 3 shows a perspective view of the assembled sensing device exemplary of the type which may be used in accordance with the instant invention. The gas sensing device includes bottom plate 1 fabricated of a suitable plastic material which does not react with the gaseous constituents. Plate 1 has a pair of gas flow ports, 2 and 3, to allow a gas stream containing the constituent or constituents to be sensed, to be brought into a sensing chamber, not shown in FIG. 3, which communicates with the catalytic graphite sensing electrode, also shown in FIG. 3, positioned on the near surface of a hydrated, solid polymer electrolyte membrane 4 which preferably is a sulfonated perfluorocarbon cation exchange membrane. Plate 1 also has an opening 5 covered by a barrier film 6 which communicates, in the preferred embodiment, with a catalytic reference electrode, not shown in FIG. 3, positioned on the same surface of the solid polymer electrolyte membrane as the catalytic graphite sensing electrode. The catalytic reference electrode is an air/$O_2$ electrode, and in order that reversability of the air/$O_2$ electrode is optimized, the reference electrode and its active surface area should be as large as possible. The membrane area in contact with the reference area should also be fully hydrated so all of the catalyst is in contact with a highly dissociated sulfonic acid group in the solid polymer electrolyte membrane. This permits full use of the full membrane/solid polymer electrolyte area. This sensing device without the improvements of the present invention is fully described in U.S. Pat. No. 4,171,253 and is illustrated as FIG. 1 therein. Positioned on the far side of membrane 4 is a gasket 7 which is rigidly secured to the membrane by doublesided adhesive tape. Gasket 7, as explained above, includes a pair of circular hydration ports which communicate with a reservoir 8 to maintain selected portions of the far side of solid polymer electrolyte membrane 4 flooded with distilled water to permit transport of water in the vapor phase across the membrane to the sensing electrode to permit humidification of the incoming gases to bring them to high relative humidity, preferably 100%. Reservoir 8 contains a fluid filler cap or closable port shown generally at 9 which allows the introduction of distilled water which is used for flooding the far surface of solid polymer electrolyte membrane 4.

Illustrated in conjunction with FIG. 3 is a gas filtration or scrubber cartridge generally shown as 40. Although the present invention is not limited to any particular filtration or scrubber device or to any particular filtration medium and in certain instances requires no filtration or scrubber cartridge, the exemplary scrubber cartridge 40 comprises cylindrical tube 39 which may be made of glass or a suitable plastic material having an inlet tube 37 and an outlet tube 36. Outlet tube 36 is connected by suitable means, e.g. glass tubing, to flow port 3 so that filtered or scrubbed gas can exit from filter or scrubber 40 and thereafter enter the sensing device at port 3 for detection, sensing and/or measuring. Cylindrical member or tube 39 contains a suitable filtration medium 35 for filtering unwanted gases as described above. For example, filtration medium 35 may be a filter paper medium upon which a 0.1 molar aqueous mercuric chloride ($HgCl_2$) has been dried or immobilized; or it may be a triethanolamine adsorbed upon charcoal; or in certain cases it may be an activated alumina impregnated with potassium permanganate, and the like. In certain cases, the filtration or scrubber device may be mounted by a suitable clamping device 34 to the cell or to any support. In certain embodiments, the filtration or scrubbing device 40 may be mounted vertically with an inlet tube and an outlet tube in the same end, one of the tubes extending to the bottom of the scrubbing or filtration device so that it is submerged beneath a scrubbing liquid contained therein to remove or filter out undesirable gases. In this embodiment (not shown), the gas to be filtered is bubbled into a liquid filtration medium, exits from the filtration or scrubber device by the outlet port of the scrubber and enters the inlet port of the sensing device having a catalytic graphite sensing electrode.

Pump 38 is diagramatically illustrated in FIG. 3 and provides means for passing the gaseous sample containing the gas or gases to be detected and/or measured to the catalytic graphite sensing electrode in the electrochemical gas sensing cell having a hydrated, solid polymer electrolyte ion transporting membrane. This is one example of suitable means for exposing the sensing electrode to a gas to be sensed. Other suitable means can be devised by persons skilled in the art. In the embodiment shown, gas passes from a suitable inlet in the pump, through an outlet therefrom and into inlet port 37 of scrubber or filtration device 40. In certain cases where it is not necessary to remove interferent gases from the stream of gas to be detected and/or measured, filtration or scrubber device 40 is not necessary, and the outlet pump 38 may be connected directly to inlet port 3 of the electrochemical gas sensing cell.

Materials of which the cell is constructed should be those materials which are resistant or inert to the various gases to which the cell will be exposed. The current collectors may also be of any suitable material including platinized niobium screens, titanium expanded screens coated with $RuO_x$, $IrO_x$, transition metal oxides and mixtures thereof attached to a titanium plate, or a bonded noble metal or noble metal oxide clad screen attached to a palladium-titanium plate. Other metals may include nickel, mild steel or stainless steel screens.

Electrochemical sensing cells similar to the device shown in FIGS. 1 and 3 were used to test the present invention. The cells incorporated a cation exchange membrane made of hydrated co-polymer of polytetrafluoroethylene and polysulfonyl fluoride vinyl either containing pendant sulfonic ($SO_3$) acid groups. The membranes were hydrated by soaking them in water at 32° C. for thirty minutes. A Teflon bonded, catalytic graphite sensor electrode was embedded in the membrane. A platinum/5% iridium cathode and a platinum 5% iridium air ($O_2$) reference electrode were used. Various gases including nitric oxide (NO), air ($O_2$), carbon monoxide (CO), nitrogen dioxide ($NO_2$) and chlorine ($Cl_2$) were tested in the device at various applied voltages. Tables III and IV below show the analytical selectivity in microamps for gases at several applied voltages in the electrochemical cell using catalytic graphite sensing electrodes. As described above the electrochemical sensor cell was self-humidified, and the background signal with impurity-free ambient air was highly invariant over the temperature of 1° to 40° C. When used in a potentiostatic mode similar to that described in U.S. Pat. No. 4,123,700 and briefly illustrated herein in FIG. 2, it was determined that this device with the catalytic graphite sensing electrode can be used for the detection and/or measurement of easily oxidizable or reducible gases. A distinct feature of this electrochemical gas detecting and/or measuring device is that the catalytic sensing electrode contains no noble metal catalyst and is highly selective to many noxious gases in the presence of other gases such as carbon monoxide, ethylene, acetylene and the like.

The gases were tested at applied potentiostatic voltages of +0.6 to +1.5 volts relative to a standard hydrogen electrode. The active area of the test cells was approximately 1.5 cm². Signal response is designated as analytical selectivity in microamps in Table III shown below. Sample flow rate was 80 cc/minute. Chlorine gas was tested at applied potentiostatic voltages of +0.70 volt to 1.35 volts relative to a standard hydrogen electrode in a test cell as described above. Signal response is also designated as analytical selectivity in microamps in Table IV below.

TABLE III

Analytical Selectivity in Microamps (μA) for Gases at Applied Voltages (Electrochemical Cell Potentials) Using Catalytic Graphite Sensing Electrodes

| *APPLIED VOLTAGE | 55 PPM NO | AIR | 100 PPM CO | 21 PPM NO₂ |
|---|---|---|---|---|
| 1.5 | 265 | 38 | 40 | 38 |
| 1.4 | | | | |
| 1.3 | 132 | 4 | 4 | 4 |
| 1.2 | | | | |

TABLE III-continued

Analytical Selectivity in Microamps (μA) for Gases at Applied Voltages (Electrochemical Cell Potentials) Using Catalytic Graphite Sensing Electrodes

| *APPLIED VOLTAGE | 55 PPM NO | AIR | 100 PPM CO | 21 PPM NO₂ |
|---|---|---|---|---|
| 1.1 | 17 | 4 | 3 | 3 |
| 1.0 | | | | |
| 0.9 | 0 | 0 | 1 | −7 |
| 0.8 | 0 | 0 | 0 | −27 |
| 0.7 | −3 | −2 | −2 | −41 |
| 0.6 | −6 | −46 | −48 | −95 |

*vs. standard hydrogen electrode in the same solution

TABLE IV

Analytical Selectivity in Microamps (μA) for Chlorine Gas at Applied Voltages Using Catalytic Graphite Sensing Electrodes

| | Analytical Selectivity | | |
|---|---|---|---|
| *APPLIED VOLTAGE | 5 PPM Cl₂ (in microamps) | AIR (in microamps) | 100 PPM CO (in microamps) |
| 1.35 | +2 | | |
| 1.25 | −1 | | |
| 1.15 | −5 | | |
| 1.10 | −6 | 4 | 3 |
| 1.05 | −3 | | |
| 1.00 | −1 | | |
| 0.95 | −3 | | |
| 0.90 | −5 | 0 | 1 |
| 0.85 | −9 | | |
| 0.80 | −11 | 0 | 0 |
| 0.75 | −12 | | |
| 0.70 | −10 | −2 | −2 |

*vs. standard hydrogen electrode in the same solution

The data in Table IV shows that a fixed potential within the range of about 0.75 volt to about 0.90 volt versus a standard hydrogen electrode can be applied to the sensing electrode to detect chlorine gas in a cathodic reduction mode. It can also be seen in Table IV that in the applied voltage range of about 0.75 to about 0.90 volts, carbon monoxide and air are close to 0.0 microamps in analytical selectivity and therefore have little or no effect upon the analytical selectivity of the chlorine gas being detected and/or measured. At fixed potentials between about 0.75 volt to about 0.90 volt the signal to noise ratio is best when the sensor cell of this invention is used to detect chlorine. Response level generally decreases above about 0.90 volt, and there is background interference, e.g., from nitrogen dioxide reduction, below about 0.75 volt. Thus, unless the nitrogen dioxide gas is filtered from the sample being measured or detected the preferred lower applied voltage for chlorine gas detection is about 0.75.

The best operating voltage for nitric oxide (NO) detection, with minimal background contribution from air is about 1.3 volts relative to a standard hydrogen electrode. However, with a background current compensating circuit as shown in FIG. 5, voltages up to 1.5 or higher can be used for NO detection. Nitrogen dioxide ($NO_2$) is not reactive at this voltage when the catalytic graphite sensing electrode is used. Also carbon monoxide, acetylene and ethylene are electrochemically non-reactive on the electrode at this potential over the temperature range of 1°–40° C.

The best operating voltage for nitrogen dioxide ($NO_2$) detection with minimal background contribution from air appears to be 0.7 volt. However, with a background current compensating circuit as shown in FIG. 5, voltages as low as 0.6 volt or lower can be used for $NO_2$ detection. There is minimal interference from hydrogen sulfide ($H_2S$) or sulfur dioxide ($SO_2$) at this voltage. As explained above, any interferent gases can be removed from the gaseous stream undergoing detection and/or measurement by filtration. Filtration media have been discussed above, and in many cases may also be achieved by using immobilized salts, such as immobilized salts of silver ($Ag^+$), lead ($Pb^{++}$) for hydrogen sulfide or by weak alkaline bicarbonate ($HCO_3^-$), citrate and the like species for sulfur dioxide. As discussed above, immobilized mercuric salts appear useful for the removal of the sulfur species.

Figure 4A:
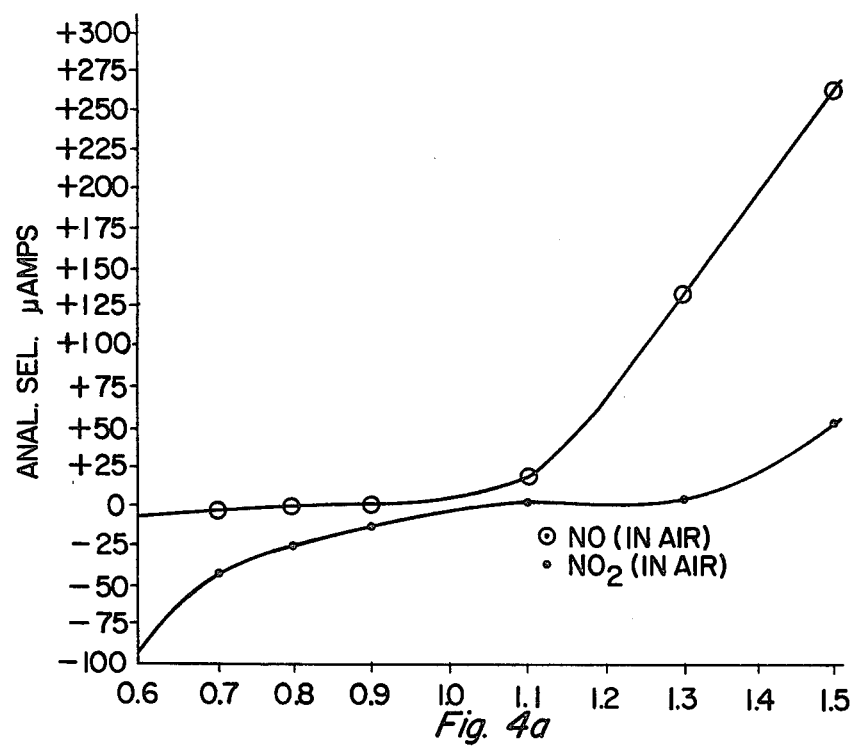
FIGS. 4a, 4b and 4c are graphs showing the analytical selectivity of the electrochemical gas sensing device of the present invention for the oxides of nitrogen, air and CO at specified applied voltages.

The applied voltages of Table III in analytical selectivity for NO and $NO_2$ have been plotted in the form of a graph and are shown in FIG. 4a. By using the graphs in FIGS. 4a, 4b and 4c, a range of voltages suitable for electrochemical reduction or electrochemical oxidation of a particular gas can be easily selected. Thus, for nitric oxide (NO) gas, a fixed potential within the range of about 1.1 to about 1.3 volts versus a standard hydrogen electrode can be selectively applied to the sensing electrode to detect nitric oxide gas in an anodic oxidation mode. To detect and/or measure nitrogen dioxide, it can be seen from the graph of FIG. 4a that a fixed potential within the range of about 0.7 to about 0.9 volt versus a standard hydrogen electrode can be used for selectively applying a voltage to the sensing electrode to detect nitrogen dioxide ($NO_2$) gas in a cathodic reduction mode. It can also be seen from the graph of FIGS. 4b and 4c that at an applied voltage from about 0.7 to about 1.3 volts, carbon monoxide and air are close to 0.0 microamps in analytical selectively and therefore have little or no effect upon the analytical selectivity of the gases being detected and/or measured.

Figure 4B:
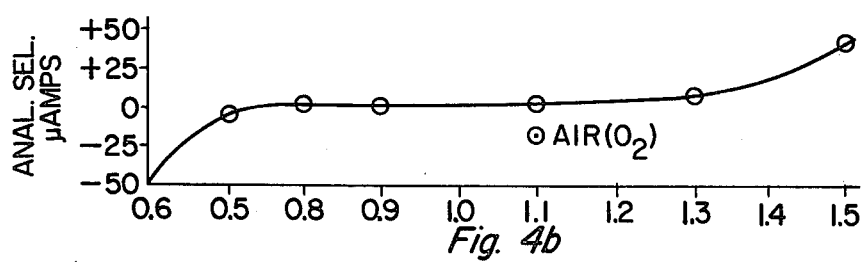
Figure 4C:
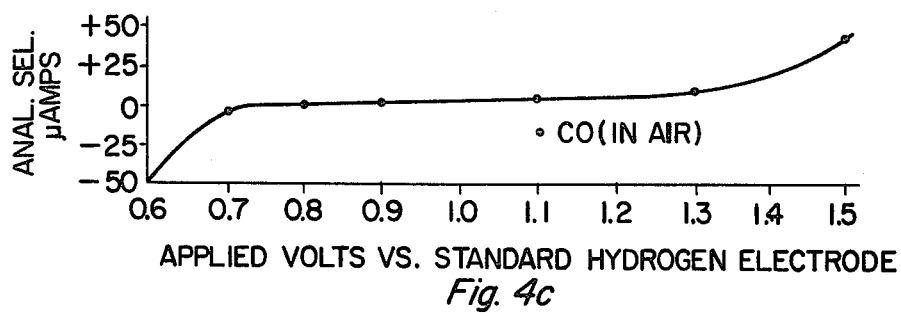

FIG. 4b shows the response curve for oxygen alone (air) at the same applied voltages shown in FIG. 4a. FIG. 4c shows the response curve for carbon monoxide alone at the same applied voltages shown for FIG. 4a. Viewing the curves in FIGS. 4a, 4b and 4c simultaneously, explains why the NO response curve shows current flow under certain cathodic conditions, i.e., applied voltage less than 0.7 volt, and why the $NO_2$ response curve shows current flow under certain anodic conditions, i.e., applied voltage greater than 1.3 volts. Thus, the preferred operating voltages for NO detection are below about 1.3 volts (1.1–1.3 volts) and for $NO_2$ detection are above about 0.7 volt (0.7–0.9 volt). As explained above, at voltages above 1.3 volts and below 0.7 volt, the background current due to the air (oxygen) may be subtracted for accurate readings.

From the data in the graphs of FIGS. 4a, 4b and 4c, it can be easily seen that the operating range of this electrochemical gas sensing device and process is within the range of about 0.7–1.3 volts relative to a standard hydrogen electrode in a device which utilized a solid polymer electrolyte and a catalytic graphite sensing electrode. This range can be extended by utilizing a background current compensating means for oxygen interference below 0.7 volt and above 1.3 volts. No corrosive liquid electrolytes are required and excellent sensitivity has been shown without the use of expensive sensing electrodes. Thus, it will be appreciated that a vastly superior electrochemical gas sensing device and process for detecting and/or measuring noxious gases has been demonstrated. There is no interference from carbon dioxode, acetylene, ethylene, air ($O_2$) and the like when the catalytic graphite sensing electrode is used in electrical contact with a solid polymer electrolyte ion transporting membrane in an electrochemical cell in accordance with the present invention. The inexpensive catalytic graphite electrode has excellent selectivity as well as excellent sensitivity to the noxious gases, nitric oxide (NO), nitrogen dioxide ($NO_2$) and chlorine ($Cl_2$). Furthermore, in accordance with the present invention, there is no dissolution of precious metals at the catalytic sensing electrode.

While the instant invention has been shown in connection with preferred embodiments thereof, the invention is by no means limited thereto, since other modifications of the apparatus and devices employed and the steps of the process may be made and fall within the scope of the invention. It is contemplated by the appended claims to cover any such modifications that fall within the true scope and spirit of this invention.

What is claimed is:

1. In an electrochemical gas-sensing device of the type having a hydrated, solid polymer electrolyte ion transporting membrane, catalytic sensing and reference electrodes positioned on one side of the membrane and a counter electrode positioned on the opposite side of the membrane, said electrodes being bonded to the ion transporting membrane, means for exposing the sensing electrode to a gas to be sensed and means for measuring a current which flows between the sensing and counter electrodes while a voltage applied to the sensing electrode is maintained constant, the improvement being a sensing electrode comprising graphite bonded to the solid polymer electrolyte ion transporting membrane.

2. The gas sensing device of claim 1 wherein the graphite sensing electrode bonded to the solid polymer electrolyte ion transporting membrane is an anode for the anodic oxidation of a gas to be sensed and the counter electrode is a cathode.

3. The gas sensing device of claim 1 wherein the graphite sensing electrode bonded to the solid polymer electrolyte ion transporting membrane is a cathode for the cathodic reduction of a gas to be sensed and the counter electrode is an anode.

4. The gas sensing device of claim 1 wherein means is provided for selectively applying a voltage to the sensing electrode at a fixed potential within the range of about 0.6 to about 1.5 volts versus a standary hydrogen electrode, the applied voltage being dependent upon the gas being detected.

5. The gas sensing device of claim 1 wherein means is provided for selectively applying a voltage to the sensing electrode at a fixed potential within the range of about 0.7 to about 0.9 volt versus a standard hydrogen electrode to detect nitrogen dioxide ($NO_2$) gas in a cathodic reduction mode.

6. The gas sensing device of claim 1 wherein means is provided for selectively applying a voltage to the sensing electrode at a fixed potential within the range of about 1.1 to about 1.3 volts versus a standard hydrogen electrode to detect nitric oxide (NO) gas in an anodic oxidation mode.

7. The gas sensing device of claim 1 wherein means is provided for selectively applying a voltage to the sensing electrode at a fixed potential within the range of about 0.75 to about 0.90 volt versus a standard hydrogen electrode to detect chlorine ($Cl_2$) gas in a cathodic reduction mode.

8. The gas sensing device of claim 1 further comprising means for compensating for any background current due to oxygen.

9. A nitrogen dioxide ($NO_2$) gas sensing device comprising:
 (a) a hydrated, solid polymer electrolyte ion transporting membrane;
 (b) a catalytic nitrogen dioxide sensing cathode and a reference electrode on one side of the membrane, said catalytic sensing cathode comprising graphite bonded to the solid polymer electrolyte ion transporting membrane to detect nitrogen dioxide gas by the cathodic reduction of the nitrogen dioxide;
 (c) an anode positioned on the other side of the membrane, said anode being bonded to the solid polymer electrolyte ion transporting membrane;
 (d) means for exposing the catalytic sensing cathode to nitrogen dioxide gas to be detected;
 (e) means for maintaining the cathode at a fixed potential of about 0.7 to about 0.90 volt versus a standard hydrogen electrode to cause the eletrochemical reduction of the nitrogen dioxide and thereby create a current flow between the catalytic sensing cathode and the anode; and
 (f) means for detecting the current which flows between the cathode and the anode, said current being a measure of the nitrogen dioxide gas concentration.

10. The nitrogen dioxide gas sensing device of claim 9 wherein the catalytic sensing cathode further comprises an inert filler or binder blended with the graphite.

11. The nitrogen dioxide gas sensing device of claim 10 wherein the inert filler or binder is polytetrafluoroethylene.

12. The nitrogen dioxide gas sensing device of claim 9 wherein the catalytic sensing cathode further comprises about 10% to 50% by weight polytetrafluoroethylene (based upon the weight of the graphite and polytetraflurorethylene), blended with the graphite.

13. The nitrogen dioxide gas sensing device of claim 9 further comprising means for maintaining the solid polymer electrolyte ion transporting membrane in a hydrated state regardless of the relative humidity of the nitrogen dioxide gas being detected.

14. The nitrogen dioxide gas sensing device of claim 9 wherein the amount of graphite bonded to the solid polymer electrolyte ion transporting membrane to form the cathode is from about 4 $mg/cm^2$ to 10 $mg/cm^2$.

15. The nitrogen dioxide gas sensing device of claim 9 further comprising means for compensating for any background current due to oxygen below 0.7 volt versus a standard electrode and means for maintaining the cathode at a fixed potential below about 0.7 volt.

16. A nitric oxide (NO) gas sensing device comprising:
 (a) a hydrated, solid polymer electrolyte ion transporting membrane;
 (b) a catalytic nitric oxide sensing anode and a reference electrode on one side of the membrane, said catalytic sensing anode comprising graphite bonded to the solid polymer electrolyte ion transporting membrane to detect nitric oxide gas by the anodic oxidation of the nitric oxide;
 (c) a cathode positioned on the other side of the membrane, said cathode being bonded to the solid polymer electrolyte ion transporting membrane;
 (d) means for exposing the catalytic sensing anode to nitric oxide gas to be detected;
 (e) means for maintaining the anode at a fixed potential of about 1:1 to about 1:3 volts versus a standard hydrogen electrode to cause the electrochemical oxidation of the nitric oxide and thereby create a current flow between the catalytic sensing anode and the cathode; and
 (f) means for detecting the current which flows between the anode and the cathode, said current being a measure of the nitric oxide gas concentration.

17. The nitric oxide gas sensing device of claim 16 wherein the catalytic sensing anode further comprises an inert binder blended with the graphite.

18. The nitric oxide gas sensing device of claim 17 wherein the inert binder is polytetrafluoroethylene.

19. The nitric oxide gas sensing device of claim 16 wherein the catalytic sensing anode further comprises about 10% to 50% by weight polytetrafluoroethylene (based upon the weight of the graphite and polymer), blended with the graphite.

20. The nitric oxide gas sensing device of claim 16 further comprising means for maintaining the solid polymer electrolyte ion transporting membrane in a hydrated state regardless of the relative humidity of the nitric oxide gas being detected.

21. The nitric oxide gas sensing device of claim 16 wherein the amount of graphite bonded to the solid polymer electrolyte ion transporting membrane to form the anode is from about 4 $mg/cm^2$ to 10 $mg/cm^2$.

22. The nitric oxide gas sensing device of claim 16 further comprising means for compensating for any background current due to oxygen above 1.3 volts versus a standard hydrogen electrode and means for maintaining the anode at a fixed potential above about 1.3 volts.

23. A chlorine ($Cl_2$) gas sensing device comprising:
 (a) a hydrated, solid polymer electrolyte ion transporting membrane;
 (b) a catalytic chlorine sensing cathode and a reference electrode on one side of the membrane, said catalytic sensing cathode comprising graphite bonded to the solid polymer electrolyte ion transporting membrane to detect chlorine gas by the cathodic reduction of chlorine;
 (c) an anode positioned on the other side of the membrane, said anode being bonded to the solid polymer electrolyte ion transporting membrane;
 (d) means for exposing the catalytic sensing cathode to chlorine gas to be detected;
 (e) means for maintaining the cathode at a fixed potential of about 0.7 to about 0.90 volt versus a standard hydrogen electrode to cause the electrochemical reduction of the chlorine and thereby create a current flow between the catalytic sensing cathode and the anode; and,
 (f) means for detecting the current which flows between the cathode and the anode, said current being a measure of the chlorine gas concentration.

24. A method for the electrochemical detection of a gas comprising:
 (a) passing a gaseous sample containing the gas to a catalytic graphite sensing electrode in an electrochemical gas-sensing cell having a hydrated, solid polymer electrolyte ion transporting membrane, the catalytic sensing electrode and a reference electrode positioned on one side of the membrane and a counter electrode positioned on the opposite side of the membrane, said electrodes being bonded to the ion transporting membrane;
 (b) maintaining the catalytic graphite sensing electrode at a constant applied voltage; and (c) detecting current flow between the catalytic graphite sensing electrode and the counter electrode.

25. The method of claim 24 further comprising measuring current flow between the catalytic graphite sensing electrode and the counter electrode to determine the amount of gas.

26. The method of claim 24 further comprising filtering the gaseous sample for the removal of gases, other than the gas being detected, which cause a substantial current flow between the catalytic graphite sensing electrode and the counter electrode at the same constant voltage applied to the graphite sensing electrode as the gas being detected.

27. The method of claim 24 wherein the catalytic graphite sensing electrode is maintained at any constant voltage of between about 0.6 to 1.5 volts versus a standard hydrogen electrode.

28. The method of claim 24 wherein the catalytic graphite sensing electrode is the anode and the counter electrode is the cathode, and the gas is nitric oxide which is electrochemically oxidized at the anode at a voltage between about 1.1 and 1.5 volts versus a standard hydrogen electrode.

29. The method of claim 28 further comprising compensating for any background current due to oxygen above 1.3 volts versus a standard hydrogen electrode.

30. The method of claim 24 wherein the catalytic graphite sensing electrode is the cathode and the counter electrode is the anode and the gas is nitrogen dioxide which is electrochemically reduced at the cathode at a voltage between about 0.6 and 0.9 volt versus a standard hydrogen electrode.

31. The method of claim 24 wherein the catalytic graphite sensing electrode is the cathode and the counter electrode is the anode and the gas is chlorine ($Cl_2$) which is electrochemically reduced at the cathode at a voltage between about 0.75 and 0.90 volt versus a standard hydrogen electrode.

32. A method for the detection of a gas which can be electrochemically oxidized at a voltage between about 0.6 and 1.5 volts relative to a standard hydrogen electrode comprising:

(a) passing a gaseous sample containing the gas which can be electrochemically oxidized, to a catalytic graphite anode in an electrochemical gas-sensing call having a hydrated, solid polymer electrolyte ion transporting membrane, the catalytic graphite anode and a reference electrode positioned on one side of the membrane and a cathode positioned on the opposite side of the membrane, said anode and cathode being bonded to the ion transporting membrane;

(b) maintaining the catalytic graphite anode at a constant applied voltage between about 0.6 and 1.5 volts relative to a standard hydrogen electrode; and, (c) detecting current flow between the catalytic graphite anode and the cathode.

33. The method of claim 32 further comprising measuring the current flow between the catalytic graphite anode and the cathode to determine the amount of the gas being detected.

34. The method of claim 32 wherein the gas being detected is nitric oxide.

35. The method of claim 34 further comprising filtering at least one of the gases of the group consisting of nitrogen dioxide, hydrogen sulfide and sulfur dioxide from the gas being detected when at least one of the gases of said group is present with the gas being detected in the gaseous sample.

36. The method of claim 34 further comprising compensating for any background current below about 0.7 volt and above about 1.3 volts.

37. A method for the detection of a gas which can be electrochemically reduced at a voltage between about 0.6 and 1.5 volts relative to a standard hydrogen electrode comprising:

(a) passing a gaseous sample containing the gas which can be electrochemically reduced to a catalytic graphite cathode in an electrochemical gas-sensing cell having a hydrated, solid polymer electrolyte ion transporting membrane, the catalytic graphite sensing cathode and a reference electrode positioned on one side of the membrane and an anode positioned on the opposite side of the membrane, said cathode and anode being bonded to the ion transporting membrane;

(b) maintaining the catalytic graphite cathode at a constant applied voltage between about 0.6 and 1.5 volts relative to a standard hydrogen electrode; and, (c) detecting current flow between the catalytic graphite cathode and the anode.

38. The method of claim 37 further comprising measuring the current flow between the catalytic graphite cathode and the anode to determine the amount of the gas being detected.

39. The method of claim 37 wherein the gas is selected from the group consisting of nitrogen dioxide ($NO_2$) and chlorine ($Cl_2$).

40. The method of claim 39 further comprising filtering one of the gases of the group consisting of nitrogen dioxide and chlorine from the gas being detected when the other gas of said group is present with the gas being detected in the gaseous sample.

41. The method of claim 37 further comprising compensating for any background current below about 0.7 volt and above about 1.3 volts.

* * * * *